United States Patent [19]

Larson et al.

[11] Patent Number: 4,678,749

[45] Date of Patent: Jul. 7, 1987

[54] LIGANDS FOR AFFINITY CHROMATOGRAPHIC PURIFICATION OF ALDOSE REDUCTASE

[75] Inventors: Eric R. Larson, Mystic; Todd W. Siegel, Milford, both of Conn.

[73] Assignee: Pfizer Inc., New York, N.Y.

[21] Appl. No.: 930,590

[22] Filed: Nov. 13, 1986

[51] Int. Cl.$^4$ .......................... C12N 9/00; C12N 9/02; C12N 9/96

[52] U.S. Cl. .................................. 435/183; 435/188; 435/189; 525/329.4; 548/309

[58] Field of Search ................ 548/309; 435/183, 188, 435/189; 525/329.4

[56] References Cited

PUBLICATIONS

Crabbe et al., *Biochem. Soc. Trans.*, 8, 194 (1980).
Branlant, *Eur. J. Biochem.*, 129, 99–104 (1982).

*Primary Examiner*—Richard A. Schwartz
*Attorney, Agent, or Firm*—Charles J. Knuth; Albert E. Frost; Peter C. Richardson

[57] ABSTRACT

4-(S)-8-($\omega$-carboxy-1-oxoalkylamino) derivatives of sorbinil useful as ligands for affinity chromatographic purification of aldose reductase; methods for their preparation and use for the above-mentioned purpose.

13 Claims, No Drawings

LIGANDS FOR AFFINITY CHROMATOGRAPHIC PURIFICATION OF ALDOSE REDUCTASE

BACKGROUND OF THE INVENTION

1. Field of the Invention

This invention relates to 4-(S)-8-(ω-carboxy-1-oxoalkylamino) derivatives of sorbinil useful as ligands for affinity chromatographic purification of aldose reductase; to use of the derivatives and to methods for their preparation.

2. Description of Related Art

While the search for improved oral antidiabetic agents continues, considerable effort is currently directed to the discovery of compounds of value in preventing or minimizing certain chronic complications of diabetes such as cataract formation, neuropathy, nephropathy and retinopathy. Such compounds function as inhibitors of the enzyme aldose reductase which is primarily responsible for regulating the reduction of aldoses (like glucose and galactose) to the corresponding polyols (such as sorbitol and galactitol) in the human body. In this way, unwanted accumulations of galactitol in the lens of galactosemic subjects and of sorbitol in the lens, peripheral nervous cord and kidney of various diabetic subjects are thereby prevented or otherwise reduced as the case may be. As a result, such compounds are definitely of value as aldose reductase inhibitors for controlling certain chronic diabetic complications, including those of an ocular nature, since it is already known in the art that the presence of polyols in the lens of the eye invariably leads to cataract formation together with a concomitant loss of lens clarity.

The availability of high quality aldose reductase is important for the above-mentioned effort since the activity of compounds as agents for control of chronic diabetic complications is determined by measuring their ability to inhibit the activity of isolated aldose reductase [C. A. Lipinski et al., Ann. Reports Med. Chem. 19, 169 (1984)].

Crabbe et al., Biochem. Soc. Trans. 8, 194 (1980) report the purification of aldose reductase from bovine lens by means of poly[2-(diethylamino)ethyl]polyglycerylene dextran hydrochloride (DEAE-Sephadex, available from Pharmacia Fine Chemicals, Uppsala, Sweden) and affinity chromatography on cyclic AMP-Sepharose (also available from Pharmacia Fine Chemicals).

Purification of pre-purified porcine lens aldose reductase by affinity chromatography by a factor of 3× based on specific activity was reported by Branlant [Eur. J. Biochem. 129 99 (1982)].

Sorbinil, the USAN name for 2,3-dihydro-6-fluoro-spiro[4H-1-benzopyran-4,4'-imidazolidine]-2',5'-dione, and its use for the control (therapeutic and prophylactic) of diabetes-associated chronic complications are disclosed in U.S. Pat. Nos. 4,130,714 and 4,147,795.

The 8-nitro- and 8-amino derivatives of sorbinil are described in U.S. Pat. No. 4,248,882, issued Feb. 3, 1981.

Hasler et al., Med. Chem. Symp., Cambridge, England, disclose a series of 8-[(substituted aminorbonyl)amino]-2 3-dihydro-6-fluoro-spiro-chromane- 4,5-thiazolidine-2',4'-diones as aldose reductase inhibitors.

SUMMARY OF THE INVENTION

It has now been found that certain derivatives of sorbinil are, when bound to a solid support, useful as affinity ligands for the purification of aldose reductase via affinity chromatography. The compounds have formula (I):

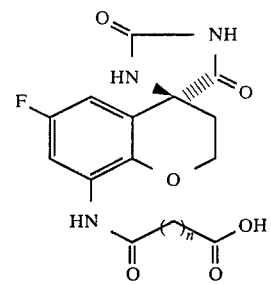

wherein n is 2, 3 or 4.

The functional; i.e., capable of participating in certain chemical reactions, substituent at the 8-position enables formula (I) compounds to bind to immobilizing polymers, and to function as ligands for the affinity chromatographic purification of aldose reductase.

Also included in this invention are intermediate compounds of formula (I-A):

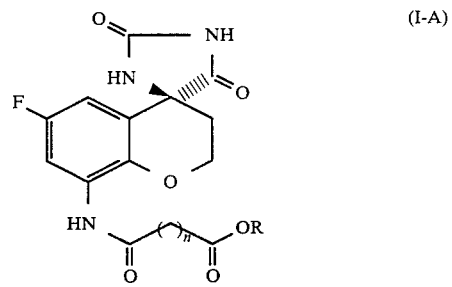

wherein n is 2, 3 or 4; and R is (C$_{1-4}$)alkyl.

The compounds of formulae (I) and (I-A) are prepared by methods known to those skilled in the art. Compounds (II) and (III) below are described in U.S. Pat. No. 4,281,882.

DETAILED DESCRIPTION OF THE INVENTION

Compounds of formula (I) are readily prepared by the sequences shown below:

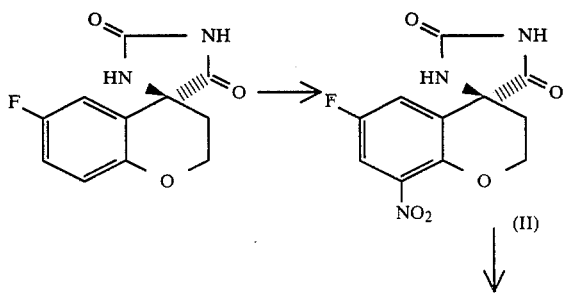

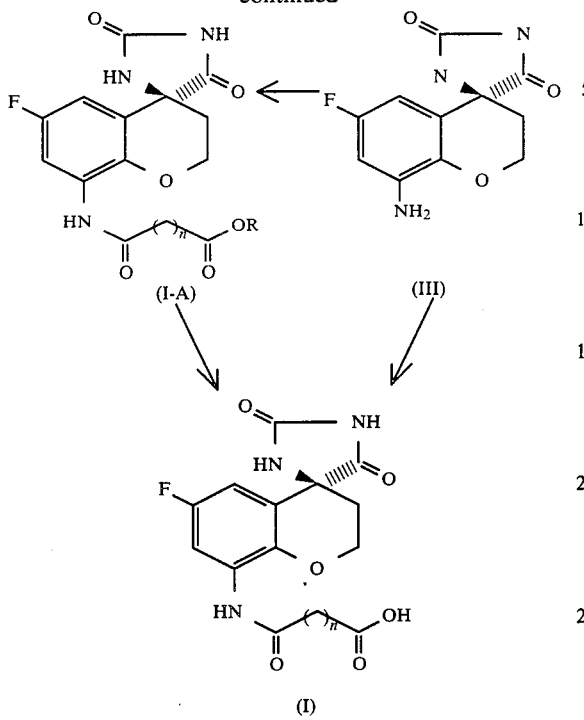

wherein n and R are as defined above.

The intermediate of formula (II) is prepared by nitration of sorbinil in concentrated sulfuric acid by means of concentrated nitric acid according to known procedures. The nitro derivative (II) is then reduced to amino derivative (III) by, for example, iron/concentrated HCl or by hydrogenation over a noble metal catalyst, such as 10% palladium-on-carbon (Pd/C). While a variety of catalysts can be used 10% Pd/C is favored since it permits use of relatively mild conditions and affords satisfactory yield of (III).

Conversion of (III) to (I-A) is accomplished by reaction of (III) with the appropriate chloroformyl derivative of formula $Cl-CO-(CH_2)_n-COOR$ wherein n and R are as defined above. The coupling is carried out in a reaction-inert solvent (tetrahydrofuran, dioxan; that is, one which does not react with reactants or desired product in a manner which reduces yield of said product); and in the presence of at least an equivalent amount of a base, preferably an organic amine. In practice an excess of the base is generally used. Suitable organic bases are triethylamine, dimethylaminopyridine, N-methylmorpholine and N,N-dimethylaniline.

The reaction is run at ambient temperature until complete. Higher temperatures can, of course, be used in which case shorter reaction times are required. Using temperatures of from about 20° C. to the boiling temperature of the reaction-inert solvent, generally requires reaction periods of from about 4 to 12 hours.

The ester of formula (I-A) is then converted to (I) by, for example, saponification in an aqueous solvent, e.g., water/dioxane using an alkali metal hydroxide (KOH). A solvent mixture is favored which provides a one-phase reaction system. Thus, water/dioxane or other reaction-inert solvent system can be used.

In an alternative process, intermediate (III) is converted directly to compounds of formula (I) wherein n is 2 or 3 by condensing (III) with succinyl anhydride or glutaryl anhydride in the presence of a catalytic base, such as a tertiary organic amine, preferably 4-(dimethylamino)pyridine. A convenient procedure comprises heating, desirably to reflux, intermediate (III) and the appropriate anhydride in a reaction-inert solvent (dioxane, tetrahydrofuran) until reaction is complete. The product is recovered by known methods. Of the two acylation methods described herein, the acid chloride procedure is favored because of the better yield of product.

Solid supports (or resins) comprising the affinity ligands of formula (I) bound thereto are prepared by coupling a formula (I) compound to a solid support (or resin) having amino or aminoalkyl groups attached to its back-bone structure. The coupling is carried out by known procedures as, for example, by dehydrative coupling using a carbodiimide such as 1-(3-dimethylaminopropyl-3-ethyl)carbodiimide.

The matrix or solid support can be any polymeric substance commonly used in ion-exchange or chromatography into which basic reactive, i.e., amino or aminoalkyl groups have been introduced. Representative supports of this type are known in the ion exchange and chromatography fields, e.g. aminoethyl-Sepharose, Bio-Gel P-300 with ethylenediamine (Biorad Laboratories, Richmond, Calif.), aminocellulose and amino group-bearing glass beads. Especially useful as solid support is N-(2-aminoethyl)polyacrylamide.

The affinant of formula (I) is bound to each of said matrices by known coupling methods, preferably in the presence of a carbodiimide.

To the affinity resin comprising formula (I) solid support prepared as described above is added an aldose reductase containing aqueous extract. In the present instance, aldose reductase was obtained from a suitable source, such as rat lenses. The extract was obtained by honogenization of lenses in the presence of a suitable buffer, followed by centrifugation to remove insolubles, the supernatant being used directly as the aldose reductase source, without further purification.

The source of the aldose reductase is immaterial. It can be, for example, from bovine lenses, human erythrocytes or lenses, rat lenses, human placenta, porcine muscle, rabbit muscle (or other tissues from which the enzyme or isolated by conventional techniques).

The present invention is illustrated by the following examples. It will be understood, however, that the invention is not limited to the specific details of these examples.

EXAMPLE 1

4-(S)-2,3-Dihydro-6-Fluoro-8-Nitro-Spiro-(4H-1-benzopyran-4,4'-imidazoline)-2',5'-dione To a suspension of 4-(S)-2,3-dihydro-6-fluorospiro(4H-1-benzopyran-4,4'-imidazoline)-2',5'-dione (Sorbinil, 3.54 g., 15 mmol) in 80 ml. ice cold concentrated $H_2SO_4$ was added 2 ml. of 90% $HNO_3$ (d=1.5) dropwise. After 15 minutes, the reaction was poured onto 1.5l ice/$H_2O$ and extracted with 5×250 ml. ethyl acetate. The combined extracts were dried over anhydrous $Na_2SO_4$, filtered and evaporated to give a 42% yield (1.77 g.) of title compound as a yellow solid.

NMR (90 MHz) 11.2–10.9 (1H, br); 8.65–8.48 (1H, br); 7.85 (1H, dd, J=3 Hz, 10 Hz); 7.38 (1H, dd, J=3, 10 Hz); 4.67–4.15 (2H, m); 2.38–2.10 (2H, m) ppm.

IR (KBr) 3350, 3203, 1767, 1726, 1591 $cm^{-1}$.

MS (m/e) 281.1, 237.0, 210.0, 182.0.

EXAMPLE 2

4-(S)-8-amino-2,3-dihydro-6-fluoro-spiro-(4H-1-benzopyran-4,4'-imidazoline)-2',5'-dione A solution of 5.05 g. (20 mmol) of the product of Example 1 in 150 ml. ethyl acetate containing 500 mg. of 10% Pd/C was shaken under 3 atmospheres (50 psi) H2 for 52 hours. The reaction was filtered and the filtrate evaporated to give an 88% yield (3.98 g.) of the title compound as a tan powdery solid.

NMR 11.98–11.88 (1H, br); 8.54 (1H, s); 6.35 (1H, dd, J=3 Hz, 10 Hz); 5.92 (1H, dd, J=3 Hz, 10 Hz); 5.20 (2H, s); 4.47 (1H, "t", J=9 Hz); 4.16 (1H, "t", J=9 Hz); 2.23 (1H, m); 2.08 (1H, m) ppm.

IR (KBr) 3386, 3223, 1778, 1719, 1622 cm$^{-1}$.

HRMS Calcd. for $C_{11}H_{10}N_3O_3F=251.0710$; Found=251.0709.

MS m/e 250.9, 223.0, 180.0, 152.0.

EXAMPLE 3

4-(S)-8-(4-carbomethoxy-1-oxobutylamino)-2,3-dihydro-6-fluoro-spiro-(4H-1-benzopyran-4,4'-imidazoline)-2',5'-dione To a solution of 3.98 g. (15.8 mmol) of the product of Example 2 in 50 ml. THF was added 193 mg. (1.6 mmol) of 4-dimethylaminopyridine, 6.6 ml. (47.4 mmol) triethylamine and 2.6 ml. (19 mmol) of methyl (4-chloroformyl)butyrate. After 12 hours, 50 ml. 1N HCl was added and the THF evaporated in vacuo. The residue was extracted with 3 x 75 ml. ethyl acetate. The combined extracts were dried over Na2SO4, filtered, and evaporated to a gold foam, which was purified via flash column chromatography (100% EtOAc over SiO2) yielding 6.81 g. of a white solid, which was dissolved in 175 ml. CH3OH. To this was added 1.79 (12.96 mmol) of powdered anhydrous K2CO3, and the reaction heated under reflux for 3 hours. The CH3OH was evaporated and the residue dissolved in 150 ml. ethyl acetate, which was washed with water (100 ml.), dried over Na2SO4, filtered and evaporated to give an 83% yield (4.97 g.) of title product.

NMR 9.32 (1H, s); 8.60 (1H, s); 7.86 (1H, dd, J=3 Hz, 10 Hz); 6.60 (1H, dd, J=3 Hz, 10 Hz); 4.56 (1H, m), 4.26 (1H, m); 3.58 (3H, s); 2.50–2.40 (2H, m); 2.40–2.20 (2H, m); 2.20–2.06 (2H, m); 1.86–1.66 (2H, m) ppm.

EXAMPLE 4

4-(S)-8-(4-carboxy-1-oxobutylamino)-2,3-dihydro-6-fluoro-spiro-(4H-1-benzopyran-4,4'-imidazoline)-2',5'-dione Method A To a solution of 3.11 g. (8.2 mmol) of the product of Example 3 in 200 ml. 1:1 H2O/1,4-dioxane was added 2.30 g. (41 mmol) of solid KOH. After 4 hours, the 1,4-dioxane was evaporated and the aqueous residue was washed with 2×50 ml. CH2Cl2, then acidified to pH=1.0 and extracted with 3×75 ml. ethyl acetate. The combined ethyl acetate extracts were dried over Na2SO4, filtered and evaporated to a gold foam, which was recrystallized from ethyl acetate/hexanes affording crystalline product in 63% yield (1.89 g.) MP=213–214 [alpha]=+65.6 (c=1.0, EtOH).

NMR 9.37 (1H, s); 8.66 (1H, s); 7.94 (1H, dd, J=3 Hz, 10 Hz); 6.66 (1H, dd, J=3 Hz, 10 Hz); 4.63 (1H, br); 4.33 (1H, t, J=9 Hz); 3.60–3.20 (1H, br); 2.53 (2H, m); 2.22 (2H, m); 1.84 (2H, t, J=9 Hz) ppm.

C13 NMR 176.4, 174.17, 171.61, 156.60, 156.19, 153.69, 141.47, 128.55, 128.42, 121.00, 120.89, 108.90, 108.51, 106.80, 106.34, 62.87, 59.31, 35.18, 32.99, 31.56, 20.48 ppm.

IR (KBr) 3230, 1777, 1721, 1624, 1532 cm$^{-1}$.

Analysis Calcd. for $C_{16}H_{16}N_3O_6F$: C, 52.61, H4.41, N11.50; Found: C, 52.47, H4.44, N11.42.

Method B

A solution of the product of Example 2 (1.25 g., 5 mmol), glutaric anhydride (800 mg., 7 mmol), 4-(dimethylamino)pyridine (100 mg.) in dry 1,4-dioxane (25 ml.) was heated under reflux for 4 hours. The mixture was then cooled, evaporated in vacuo, and the residue partitioned between diethyl ether (100 ml.) and 0.2N aqueous potassium hydroxide (35 ml.). The aqueous layer was then acidified (6N HCl) to pH2, extracted with ethyl acetate (2×50 ml.) and the combined extracts washed with water (25 ml.), saturated aqueous brine (25 ml.), dried (sodium sulfate), filtered and evaporated. Crystallization of the residue from toluene/2-propanol afforded 250 mg. of title product as a tan powder. M.p.=215° C. (dec.).

EXAMPLE 5

Following the procedure of Example 3, but using the appropriate half-acid chloride half-ester derivatives of succinic, glutaric and adipic acids affords compounds of the formula

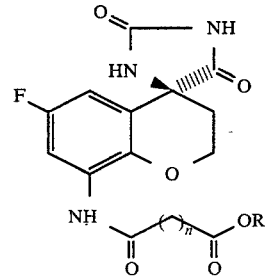

wherein n and R are:

| n | R |
| --- | --- |
| 2 | C2H5 |
| 3 | C2H5 |
| 4 | C2H5 |
| 2 | n-C4H9 |
| 3 | n-C4H9 |

EXAMPLE 6

Repetition of the procedure of Example 4A but using the products of Example 5 provides the following compounds:

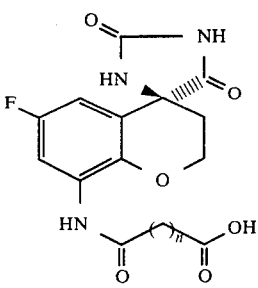

wherein n is 2, 3 and 4.

EXAMPLE 7

The procedure of Example 4-B is repeated but using succinic anhydride in place of glutaric anhydride to give:

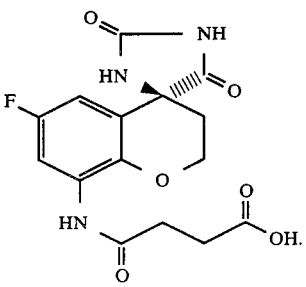

EXAMPLE 8

The sodium salt of 4-(S)-8-(4-carboxy-1-oxobutylamino)-2,3-dihydro-6-fluoro-spiro(4H-1-benzopyran-4,4'-imidazoline)-2',5'-dione is prepared by dissolving said compound in water containing an equivalent amount in moles of sodium hydroxide and then freeze-drying the mixture. In this way, the salt is obtained in the form of an amorphous powder which is freely soluble in water.

In like manner, the potassium and lithium salts are also similarly prepared, as are the alkali metal salts of all the other compounds of this invention which are reported in Example 6.

EXAMPLE 9

The calcium salt of 4-(S)-8-(4-carboxy-1-oxobutylamino)-2,3-dihydro-6-fluoro-spiro(4H-1-benzopyran4,4'-imidazoline)-2',5'-dione is prepared by dissolving said compound in water containing a stoichiometric amount in moles of calcium hydroxide and then freeze-drying the mixture. The corresponding magnesium salt is also prepared in this manner, as are all the other alkaline-earth metal salts not only of this particular compound, but also of those compounds described in Example 6.

EXAMPLE 10

Matrix Bound Affinity Ligand

45 Mg. of the product of Example 4 (the ligand) was dissolved in 25 ml. of 0.1M NaOH and then adjusted to pH 5.0 by the addition of 5M HCl. 25 Ml. of preswollen N-(2-aminoethyl)polyacrylamide, Bio-Gel P-150 (Biorad Laboratories, Richmond, Calif.) was washed with 1 L of 0.5M NaCl on a sintered glass funnel. The ligand solution was then added to the resin and 250 mg. of 1-(3-dimethylaminopropyl)-3-ethyl carbodiimide hydrochloride was added in three portions with constant mixing. The pH was maintained between 4.7 and 5.0 by the dropwise addition of 0.1M HCl. Once the pH was stable at pH 5.0, the suspension was shaken overnight at room temperature. The resin was then washed successively with 1 L of 0.1M sodium bicarbonate buffer (pH 8.0), containing 0.5M NaCl and 1 L of 0.1M sodium acetate buffer (pH 4.0), containing 0.5M NaCl on a sintered glass funnel. The efficiency of ligand incorporation was determined by high pressure liquid chromatography (pH 3 phosphate buffer (90–60%)/acetonitrile (10–40%) mobile phase, Rainin Microsorb C-18 (Rainin Instrument Co., Inc., Woburn, Mass.) reverse phase column, UV detection at 254 nm of the combined buffer washes, with incorporated ligand determined by difference. Incorporation of ligand was thus found to be 61%. The procedure yielded an affinity resin with a ligand concentration of 3.1 umoles/ml. of wet resin. The resin was stored in neutral buffer at 4° C. This material was used directly for purification of aldose reductase from crude tissue preparations as described below.

EXAMPLE 11

The matrix bound affinity ligand (resin) of Example 10 was used to enrich for aldose reductase in a crude lens extract as follows.

Preparation of Rat Lens Extract

Lenses were removed from rats and deep frozen. Purification was performed at 4° C. and the buffer used was 10mM potassium phosphate buffer, pH 7.4, containing 5 mM 2-mercaptoethanol. Thawed lenses were homogenized using a Polytron (0.4 ml. buffer per lens). The homogenate was centrifuged for 40 minutes at 40,000x g. and the pellet was discarded. The supernatant from 20 processed lenses was applied to a preequilibrated column (1.0×30 cm) of resin of Example 10, washed with 20 ml. of buffer and enzyme eluted with 4M NaCl dissolved in buffer. A 20-fold enrichment in specific activity and a 21% recovery of enzyme activity was achieved (compared to the high-speed supernatant), determined as described below.

Enzyme Assays and Assessment of Purity

Aldose reductase was assayed spectrophotometrically at 25° C. by monitoring the decrease in optical density at 340 nm over 10 minutes. Reaction mixtures contained 50 mM potassium phosphate buffer, pH 7.1, 0.1 mM β-nicotinamide adenine dinucleotide phosphate, reduced form (NADPH), 0.5 mM dl-glyceraldehyde and 0.4M ammonium sulfate in a total volume 2.0 ml. Reactions were initiated by the addition of enzyme and a unit of enzyme activity was defined as the amount of enzyme which reduces 1 umole of NADPH per minute under assay conditions. Protein was determined by the procedure (1) of Lowry et al., J. Biol. Chem. 193, 265–275 (1951) using bovine serum albumin as the standard.

Enzyme purity was assessed by calculating specific activity (unit/mg protein).

We claim:

1. A compound having the formula

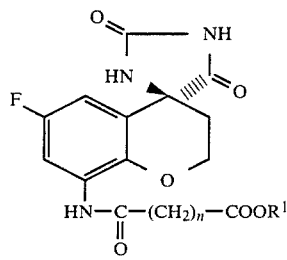

wherein n is 2, 3 or 4; and

R¹ is hydrogen or lower alkyl.

2. A compound according to claim 1 wherein n is 2.

3. A compound according to claim 1 wherein n is 3.

4. A compound according to claim 1 wherein n is 4.

5. The compound according to claim 2 wherein R¹ is hydrogen.

6. The compound according to claim 3 wherein R¹ is hydrogen.

7. The compound according to claim 3 wherein R¹ is methyl.

8. The compound according to claim 4 wherein R¹ is hydrogen.

9. An affinity resin comprising N-(2-aminoethyl)-polyacrylamide to which is coupled a compound of the formula

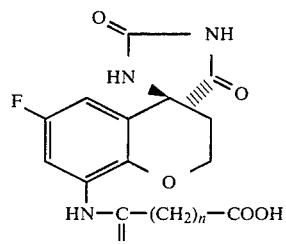

wherein n is 2, 3 or 4.

10. The resin according to claim 9 wherein n is 3.

11. A method for purification of aldose reductase from crude extracts containing it which comprises subjecting said crude extract to affinity chromatography using an aminoalkyl carrying solid support to which a compound having the formula (I)

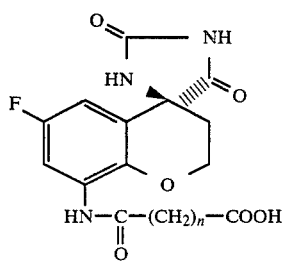

wherein n is 2, 3 or 4 has been coupled.

12. A method according to claim 11 wherein the solid support is N-(2-aminoethyl)polyacrylamide.

13. The method according to claim 12 wherein n in the formula (I) compound is 3.

* * * * *